(12) United States Patent
Lorenzo

(10) Patent No.: US 9,970,137 B2
(45) Date of Patent: May 15, 2018

(54) VARIABLE POROSITY INTRAVASCULAR IMPLANT AND MANUFACTURING METHOD

(71) Applicant: DePuy Synthes Products, Inc., Raynham, MA (US)

(72) Inventor: Juan A. Lorenzo, Davie, FL (US)

(*) Notice: Subject to any disclaimer, the term of this patent is extended or adjusted under 35 U.S.C. 154(b) by 266 days.

(21) Appl. No.: 14/883,129

(22) Filed: Oct. 14, 2015

(65) Prior Publication Data

US 2016/0032503 A1 Feb. 4, 2016

Related U.S. Application Data

(62) Division of application No. 13/795,127, filed on Mar. 12, 2013.

(51) Int. Cl.
| | |
|---|---|
| *D04C 1/06* | (2006.01) |
| *A61F 2/86* | (2013.01) |
| *A61F 2/90* | (2013.01) |
| *A61F 2/82* | (2013.01) |

(52) U.S. Cl.
CPC .......... *D04C 1/06* (2013.01); *A61F 2/86* (2013.01); *A61F 2/90* (2013.01); *A61F 2002/823* (2013.01); *A61F 2230/0004* (2013.01); *A61F 2250/0023* (2013.01); *A61F 2250/0036* (2013.01)

(58) Field of Classification Search
CPC .............. D04C 1/06; A61F 2/86; A61F 2/90
See application file for complete search history.

(56) References Cited

U.S. PATENT DOCUMENTS

| | | | | |
|---|---|---|---|---|
| 3,402,546 | A | * 9/1968 | Peene | B21F 7/00 57/215 |
| 4,567,917 | A | * 2/1986 | Millard | B29C 53/68 138/123 |
| 4,641,492 | A | * 2/1987 | Glushko | D07B 7/025 57/138 |
| 5,019,057 | A | 5/1991 | Truckai | |

(Continued)

FOREIGN PATENT DOCUMENTS

| | | |
|---|---|---|
| AU | 2005247490 A1 | 12/2005 |
| CA | 2565106 A1 | 12/2005 |

(Continued)

OTHER PUBLICATIONS

Extended European search report issued in European Application No. 14158780.8 dated Aug. 4, 2014.

(Continued)

*Primary Examiner* — Shaun R Hurley
(74) *Attorney, Agent, or Firm* — Mintz Levin Cohn Ferris Glovsky & Popeo, P.C.

(57) ABSTRACT

A vascular occlusion device for effectively occluding blood flow and pressure to a vascular defect while simultaneously not occluding blood flow and pressure to adjacent vasculature is provided. The vascular occlusion device can include a tubular member that has variable porosity regions along its length. The tubular member can be formed of a plurality of filaments that have different cross-sectional shapes along their length that are indexed to the variable porosity regions along the length of the tubular member.

11 Claims, 9 Drawing Sheets

(56) References Cited

U.S. PATENT DOCUMENTS

| | | | |
|---|---|---|---|
| 5,085,121 A * | 2/1992 | Richardson | D04C 1/06 87/29 |
| 5,111,649 A * | 5/1992 | Watakabe | D07B 1/0646 57/311 |
| 5,217,483 A | 6/1993 | Tower | |
| 5,295,346 A * | 3/1994 | Bundo | B60C 9/0007 152/451 |
| 5,395,126 A * | 3/1995 | Tresslar | F16J 15/022 277/637 |
| 5,398,586 A | 3/1995 | Akiyama et al. | |
| 5,527,354 A | 6/1996 | Fontaine et al. | |
| 5,702,373 A * | 12/1997 | Samson | A61M 25/005 604/526 |
| 5,741,325 A | 4/1998 | Chaikof et al. | |
| 5,758,562 A | 6/1998 | Thompson | |
| 5,951,599 A | 9/1999 | McCrory | |
| 6,019,786 A | 2/2000 | Thompson | |
| 6,027,526 A | 2/2000 | Limon et al. | |
| 6,093,199 A | 7/2000 | Brown et al. | |
| 6,151,879 A * | 11/2000 | Doujak | D07B 1/0606 57/1 UN |
| 6,187,036 B1 | 2/2001 | Shaolian et al. | |
| 6,214,042 B1 | 4/2001 | Jacobsen et al. | |
| 6,258,115 B1 | 7/2001 | Dubrul | |
| 6,325,822 B1 | 12/2001 | Chouinard et al. | |
| 6,361,558 B1 | 3/2002 | Hieshima et al. | |
| 6,585,758 B1 | 7/2003 | Chouinard et al. | |
| 6,685,738 B2 | 2/2004 | Chouinard et al. | |
| 6,764,505 B1 | 7/2004 | Hossainy et al. | |
| 6,835,203 B1 | 12/2004 | Vardi et al. | |
| 7,114,319 B2 * | 10/2006 | Sakonjo | B29C 70/24 57/200 |
| 7,275,471 B2 | 10/2007 | Nishri et al. | |
| 7,306,624 B2 | 12/2007 | Yodfat et al. | |
| 7,572,290 B2 | 8/2009 | Yodfat et al. | |
| 7,674,493 B2 | 3/2010 | Hossainy et al. | |
| 7,763,011 B2 | 7/2010 | Ortiz et al. | |
| 7,892,279 B2 | 2/2011 | Davidson et al. | |
| 7,938,853 B2 | 5/2011 | Chouinard et al. | |
| 7,942,925 B2 | 5/2011 | Yodfat et al. | |
| 7,959,668 B2 | 6/2011 | Yadin | |
| 8,361,104 B2 | 1/2013 | Jones et al. | |
| 2003/0139802 A1 | 7/2003 | Wulfman et al. | |
| 2004/0024416 A1 * | 2/2004 | Yodfat | A61F 2/01 606/200 |
| 2005/0098253 A1 * | 5/2005 | Doujak | D07B 1/062 152/527 |
| 2005/0149171 A1 * | 7/2005 | McCullagh | A61F 2/90 623/1.16 |
| 2005/0256563 A1 * | 11/2005 | Clerc | A61F 2/90 623/1.16 |
| 2005/0267568 A1 | 12/2005 | Berez et al. | |
| 2006/0206200 A1 | 9/2006 | Garcia et al. | |
| 2006/0206201 A1 | 9/2006 | Garcia et al. | |
| 2007/0265696 A1 * | 11/2007 | Yu | A61F 2/90 623/1.15 |
| 2009/0270974 A1 | 10/2009 | Berez et al. | |
| 2009/0287241 A1 | 11/2009 | Berez et al. | |
| 2009/0287288 A1 | 11/2009 | Berez et al. | |
| 2009/0319017 A1 | 12/2009 | Berez et al. | |
| 2010/0010624 A1 | 1/2010 | Berez et al. | |
| 2011/0054589 A1 | 3/2011 | Bashiri et al. | |
| 2012/0253377 A1 | 10/2012 | Slazas et al. | |

FOREIGN PATENT DOCUMENTS

| | | |
|---|---|---|
| CN | 101426454 A | 5/2009 |
| EP | 1750619 A2 | 2/2007 |
| JP | H09-285548 A | 11/1997 |
| JP | 2005-110779 A | 4/2005 |
| JP | 2005-514106 A | 5/2005 |
| JP | 2008502378 A | 1/2008 |
| JP | 2009-513289 A | 4/2009 |
| JP | 2009-538185 A | 11/2009 |
| JP | 2011-131086 A | 7/2011 |
| JP | 2011189141 A | 9/2011 |
| WO | WO-03057079 A1 | 7/2003 |
| WO | WO-2005115118 A2 | 12/2005 |
| WO | WO-2007139689 A2 | 12/2007 |
| WO | WO-2007139698 A2 | 12/2007 |
| WO | WO-2007139699 A2 | 12/2007 |
| WO | WO-2008063156 A2 | 5/2008 |
| WO | WO-2011025887 A1 | 3/2011 |

OTHER PUBLICATIONS

[No Author Listed] Unruptured Aneurysm, Basic Level. Mayfield Clinic & Spine Institute. www.mayfieldclinic.com. 2002. 4 pages.

Japanese Office Action issued in Japanese Application No. 2014-047324 dated Jan. 9, 2018 (Translation, 6 pages).

* cited by examiner

VARIABLE POROSITY INTRAVASCULAR IMPLANT AND MANUFACTURING METHOD

CROSS-REFERENCE TO RELATED APPLICATIONS

The present application is a divisional of U.S. application Ser. No. 13/795,127, filed on Mar. 12, 2013 and entitled "Variable Porosity Intravascular Implant and manufacturing Method," which is hereby incorporated by reference in its entirety.

BACKGROUND

Vascular disorders and defects such as aneurysms and other arteriovenous malformations often occur near the junction of large arteries, for instance at the base of the brain in the Circle of Willis. As aneurysms develop they typically form as a saccular aneurysm protruding from a wall of a vessel and have a neck and a dome portion. Alternatively, aneurysms can form as fusiform malformations that balloon a cross-section of the affected vessel.

As an aneurysm develops, the arterial internal elastic lamina disappears at the base of the neck portion, the media thins, and connective tissue replaces smooth-muscle cells. As the aneurysm is continually subjected to vascular blood pressure and blood flow, the aneurysm will grow outwardly from the wall of the vessel, which can cause pressure on the surrounding tissue as the sac or fusiform contacts the surrounding tissue. When the malformation occurs in the brain, this pressure can lead to serious mass effects, such as cognitive impairment, loss of vision, and nerve palsies. Additionally, as the aneurysm is subject to vascular blood pressure and blood flow, the walls of the aneurysm weaken, usually in the dome portion, which can eventually cause the aneurysm to tear or rupture. Ruptured aneurysms are the most common cause of subarachnoid hemorrhages, which have a mortality rate of approximately 50%.

Aneurysms and other malformations are especially difficult to treat when located near critical tissue or where ready access to the malformation is not available. Both difficulty factors apply especially to cranial aneurysms. Surgical methods have developed to treat cranial aneurysms and generally include eliminating blood flow to the aneurysm by placing a clip around the neck of a saccular aneurysm or by blocking off a fusiform aneurysm by cliping both ends of the fusiform and detouring blood flow around the secluded fusiform through an implanted vessel graft. Due to the sensitive brain tissue surrounding cranial blood vessels and the restricted access, it is challenging and risky to surgically treat defects of the cranial vasculature.

Alternatives to such surgical procedures include endovascular delivery of an implantable device, such as a stent-like device or embolic coil, through a microcatheter delivery device. In one such procedure to treat a saccular-form cranial aneurysm, the distal end of an embolic coil delivery catheter is initially inserted into non-cranial vasculature of a patient, typically a femoral artery in the groin, and guided to the aneurysm. The aneurysm sac is then filled with embolic material, such as platinum coils, that forms a solid, thrombotic mass that protects the vessel walls from blood pressure and flow. This treatment method is advantageous in that it only occludes blood flow to the aneurysm leaving the surrounding portions of the vessel unobstructed. However, it cannot treat fusiform aneurysms, and the aneurysm volume is permanently maintained.

Another technique involving the use of an intravascular implant delivers, by a microcatheter, an occlusive device in the form of a tubular, stent structure. Stents can be braided, woven, or wound from various filaments, such as a wire or wires, laser-cut from metal, or made in various other ways. They can either be self-expanding or can be expanded by another device such as a balloon. What most have in common is radial symmetry, i.e., a uniform porosity, meaning that they do not cover one portion, side, or radial sector of the vessel more or less porously than other sectors. Their symmetric construction, and therefore coverage of vessel walls, is relatively homogeneous around any given transverse slice or cross-section.

This homogenous structure can be disadvantageous in that such stents not only occlude or block blood flow to the aneurysm, but they also block blood pressure and flow along the entire length of the stent, which often impedes flow into surrounding joined vessels, such as perforator-type vessels branching off of the parent vessel. The use of a non-discriminatory occlusive device in this type of vessel can cause unintended harm to the patient if the openings, or ostia, of the perforator vessels are blocked.

Some have developed selectively-occlusive devices that discriminately block flow to an aneurysm while simultaneously allowing flow to surrounding vessels. These attempts to create discriminate occlusion devices have used multi-layered devices, varied the amount of filaments along the length of the intravascular implant, or changed the picks per inch along the length of the intravascular implant. But, generally, these devices face difficulties in manufacturing and increased costs due to difficulties in creating the multiple layers or variations in the number of filaments to create the varied porosity regions.

Accordingly, there remains a need for a device that effectively occludes a neck or fusiform of an aneurysm or other arteriovenous malformation in a parent vessel without blocking flow into perforator vessels communicating with the parent vessel that is structurally sound and easily manufactured.

SUMMARY

A vascular occlusion device for effectively occluding blood flow and pressure to a vascular defect while simultaneously not occluding blood flow and pressure to adjacent vasculature is provided. The vascular occlusion device can include a tubular member that has variable porosity regions along its length. The tubular member can be formed of a plurality of filaments that have different cross-sectional shapes along their length that are indexed to the variable porosity regions along the length of the tubular member.

In some embodiments, the vascular occlusion device includes a tubular member formed from a plurality of braided filaments. The braided filaments can define an outer surface having a mesh pattern with mesh openings defined by the braided filaments. The tubular member can have a first porosity region along a first length portion of the tubular member and a second porosity region along a second length portion of the tubular member. The porosity of the first porosity region can be less than the porosity of the second porosity region. The first porosity region can include filaments having a different shape than the filaments in the second porosity region and the tubular member can have a constant pick count throughout its length. In another embodiment the tubular member can have a braid angle that is substantially similar throughout the tubular member.

In some embodiments, the tubular member is an intravascular stent, which can be radially compressible. The first length portion is at an intermediate portion of the tubular member proximal to a distal end of the tubular member and distal to a proximal end of the tubular member. The second length portion can be adjacent to the distal end of the tubular member and/or the proximal end of the tubular member. The first length portion of the tubular member can extend over a distance in the range of about 5 mm to about 25 mm. The first porosity region can include filaments having a flattened cross-sectional shape having a length, a width, and a thickness. The width can be greater than the thickness and less than the length of the filaments in the first porosity region having a flattened cross-sectional shape. The width of the filaments having a flattened cross-sectional shape is in the range of about 0.001 inches to about 0.05 inches. The thickness of the filaments having a flattened cross-sectional shape is in the range of about 0.0003 inches to about 0.010 inches. The filaments having a round cross-sectional shape can have a diameter in the range of about 0.0005 inches to about 0.0100 inches.

The filaments in the first porosity region can be exclusively of a flattened cross-sectional shape, or can be a mixture of filaments with a flattened cross-sectional shape and/or round cross-sectional shape. The filaments in the second porosity region can have a round cross-sectional shape. The mesh openings formed from the braided filaments can have a polygonal shape and the mesh openings of the first porosity region can be smaller than the mesh openings of the second porosity region. The mesh openings of the first porosity region can have an inscribed circle diameter in the range of about 10 µm to about 500 µm and the mesh openings of the second porosity region have an inscribed circle diameter in the range of about 400 µm to about 1000 µm. The number of filaments forming the tubular member can be in the range of about 8 to about 288. For example, the number of filaments forming the tubular stent can be selected from the group consisting of 8, 16, 32, 48, 64, 72, 96, 120, 144, 192, and 288.

In another aspect, a method of manufacturing a tubular intravascular implant includes providing a plurality of supply spools, each having a supply of a filament having a round cross-sectional shape. The method further includes advancing the filaments on each supply spool to a corresponding collection spool and deforming a selected number of the filaments in a selected region thereof at selected intervals between the supply spools and the collection spools. The filaments can be deformed such that at least some of the collection spools have filaments with a round cross-sectional shape and a flattened cross-sectional shape. According to the method, the filaments in the collection spools are utilized in a filament braiding device to form a tubular member with an outer surface defined by the braided filaments. All of the collection spools used in the braiding device can have filaments with a flattened cross-sectional shape, or alternatively only a portion of the collection spools used in the braiding device can have filaments with a flattened cross-sectional shape.

The tubular member formed by the method can have a length with regions of a first, lower porosity and regions of a second, higher porosity. The method can also include the step of cutting the tubular member to form a plurality of intravascular stents; each sent having a first length region of a first, lower porosity characterized by the presence of filaments having a flattened cross-sectional shape. The intravascular stents can each have at least one second length region of a second, higher porosity characterized by the presence of filaments having a rounded cross-sectional shape.

BRIEF DESCRIPTION OF DRAWINGS

This invention will be more fully understood from the following detailed description taken in conjunction with the accompanying drawings, in which.

DETAILED DESCRIPTION

Figure 1:
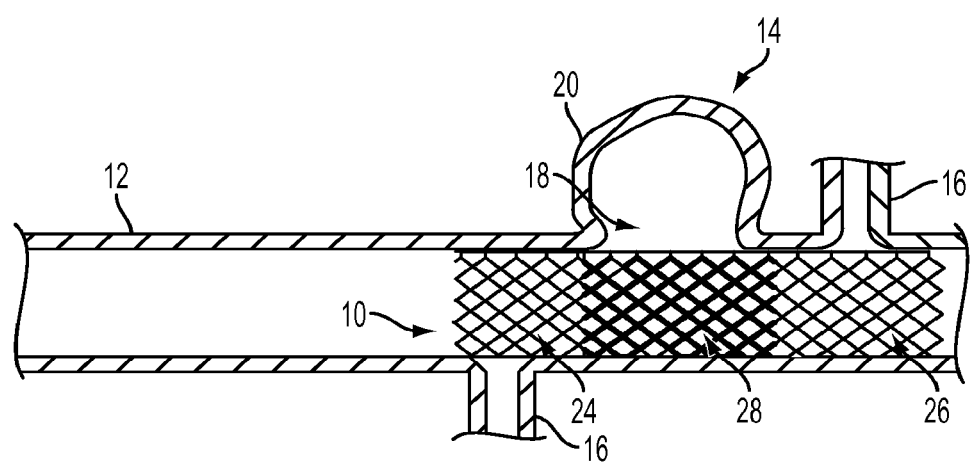
FIG. 1 is a cross-sectional view of an exemplary vascular occlusive device implanted within a vessel having a saccular aneurysm.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

To treat vascular disorders and defects, such as aneurysms and other arteriovenous malformations, intravascular implants, such as stents, can be implanted to span a length of vessel containing the defect to occlude blood pressure and flow to the defect. For instance, a stent can be delivered to the site of an aneurysm and positioned in such a manner as to occlude blood pressure and flow to the aneurysm walls. By occluding, i.e., blocking or obstructing, blood flow to the aneurysm, the risk of the aneurysm rupturing is reduced. But, in treating the vascular defect, it is important to avoid unnecessary occlusion of blood flow and pressure to adjacent vascular tissue, such as perforator vessels.

The present disclosure relates to a vascular occlusion device, such as a variable porosity stent, that is configured to occlude flow to a vascular defect while allowing flow to adjacent vessel tissue. The device utilizes a tubular member formed from a plurality of braided filaments. As explained below, the tubular member can include an outer surface having a mesh pattern with mesh openings defined by the braided filaments. The tubular member is constructed such that the porosity varies at different regions along the length of the member. For example, the tubular member can have a first porosity region along a first length portion of the tubular member and a second porosity region along a second length portion of the tubular member. In some embodiments, the first porosity region is a center portion of the tubular member. The first porosity region can include filaments having a different shape than the filaments in the second porosity region. By changing the shape of the filaments at selected regions along the length of the tubular member, the porosity of a given region can be altered while maintaining a constant pick count throughout the length of the stent. For example, the cross-sectional shape of the filament in the first porosity region can be selected to be different than the cross-sectional shape of the filament in the second porosity region so as to have a lower porosity in the first porosity region than the second porosity region. In this manner it is possible to vary the porosity from the first region to the second region by changing only the shape of the filaments, holding the other structural characteristics of the tubular member substantially constant along the length of the tubular member. That is, the number of filaments, pick count, braid angle, or braid pattern is the same in the first porosity region as in the second porosity region.

Figure 2:
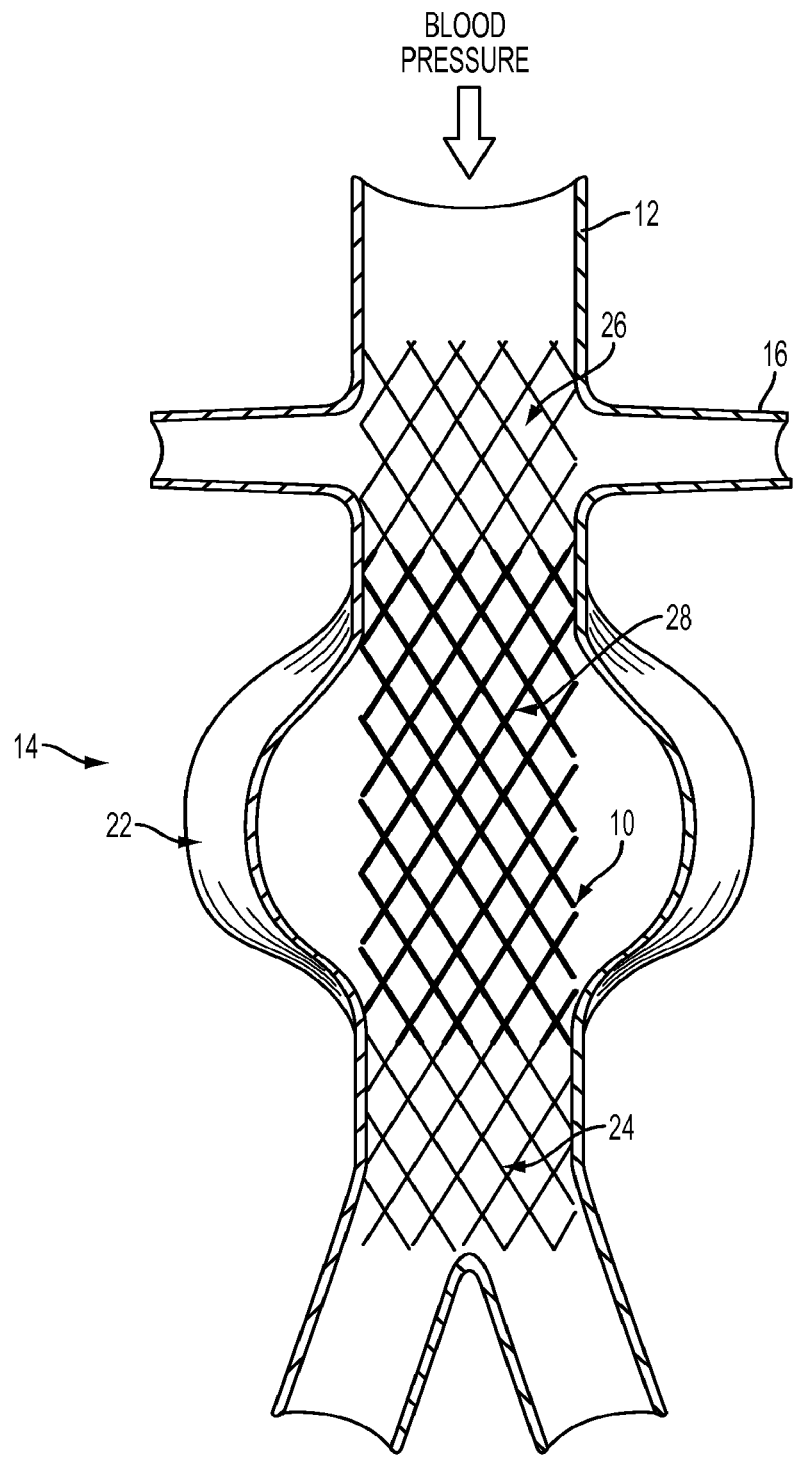
FIG. 2 is a cross-sectional view of an exemplary vascular occlusive device implanted within a vessel having a fusiform aneurysm.

FIGS. 1 and 2 illustrate embodiments wherein a variable porosity stent 10 is placed within a vessel 12 so as to occlude or obstruct blood flow and pressure to a vascular defect 14 while simultaneously allowing substantially unimpeded blood flow and pressure to adjacent vessel tissue, such as perforator vessels 16. The vessel 12 can be any vasculature, for example a cranial blood vessel such as those found in the Circle of Willis. As shown in FIG. 1, the vascular defect 14 can be a saccular form aneurysm having a neck 18 and a dome portion 20. As shown in FIG. 2, the vascular defect 14 can be a fusiform aneurysm wherein a cross-sectional portion 22 of the vessel 12 is ballooned in a radial direction. In treating either the saccular aneurysm of FIG. 1 or the fusiform aneurysm of FIG. 2, the vascular occlusion device is placed along the length of the defective vessel 12 to occlude blood flow and pressure to the aneurysm walls 20, 22.

Figure 3:
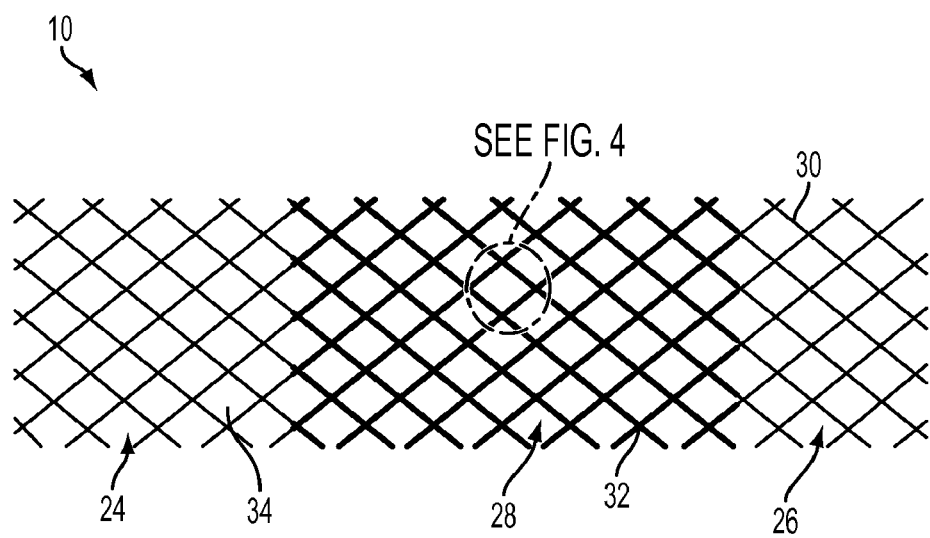
FIG. 3 is a partial cross-sectional view of an exemplary vascular occlusive device.

FIG. 3 illustrates one embodiment of a tubular stent 10 used in treating the vascular defects 14 of FIGS. 1 and 2 according to the present invention. The stent 10 can have a proximal region 24, distal region 26, and center region 28, wherein the center region 28 is intermediate the proximal and distal regions 24, 26. In the embodiment shown in FIG. 3, region 28 of stent 10 represents a first porosity region having a porosity that is different (i.e., lower) than that of regions 24 and 26, which represent a second porosity region.

The difference in porosity is achieved by changing the cross-sectional shape of the filaments 30 in region 28, as explained below. The stent 10 can be a braided stent having one or more filaments 30 of stent material woven, braided, or otherwise formed into a desired tubular shape and pattern.

Figure 4:
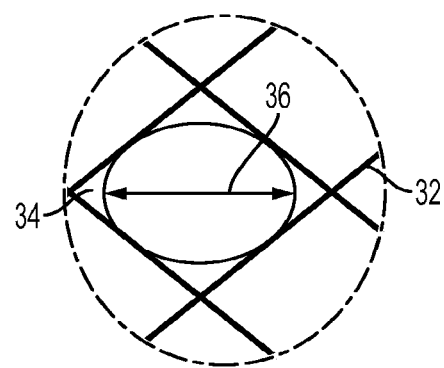
FIG. 4 is a magnified view of a portion of the device of FIG. 3.

FIG. 4 illustrates the braided, mesh structure of the stent 10. As mentioned above, the stent can be formed of braided filaments 30 that cross at junctions referred to as picks 32 to form a mesh. The mesh density is a function of the degree of spacing between the filaments 30 in the braid. Structures with more closely spaced filaments have a higher mesh density than structures with filaments that are less closely spaced. One measure of mesh density can be determined based on the number of picks 32 per inch of the material. A pick, as understood by a person skilled in the art, is a point where filaments intersect.

Porosity is a measure of the tendency of a material or structure to allow passage of a fluid therethrough. A material or structure with higher porosity has a higher fluid flow across the material than another material with lower porosity. The porosity of a braided structure, such as a stent, can be a function of the mesh density as well as the surface area of the filaments that form the structure as well as the number of filaments, the number of picks per inch, and the interstitial surface area between filaments as discussed below.

As mentioned previously, according to the present invention the cross-sectional shape of the filaments 30 can be selectively altered in certain regions, before braiding, to produce a stent 10 having a region of lower porosity. By altering the cross-sectional shape of the filaments 30, the interstitial surface area between filaments 30 can be controlled.

The interstitial surface area between filaments can be determined by measuring an inscribed circle diameter 36 (FIG. 4) in the open spaces 34 between the filaments 30. For a non-circular shape, such as a triangle, square, or diamond, the inscribed circle diameter 36 is the diameter of the largest circle that fits entirely within the shape, i.e., the diameter of a circle that is tangent to the sides of the shape. The lower porosity regions of the stent 10 can have an inscribed circle diameter 36 in the range of about 1 µm to about 400 µm, and more particularly about 100 µm. For example, the inscribed circle diameter 36 of the first porosity region 28 of the stent 10 shown in FIGS. 1-4 can be about 100 µm. The higher porosity regions, i.e., second porosity regions 24, 26, of the stent 10 can have an inscribed circle diameter 36 that is greater than about 400 µm. For example, second porosity regions 26, 24 of the stent 10 shown in FIGS. 1-4 can be in the range of about 400 µm to about 1000 µm.

To decrease the inscribed circle diameter 36 and thus decrease porosity, the cross-sectional shape of the filament 30 can be changed to increase the surface area of the filament 30 along selected portions of the filament 30 length that will correspond to the lowered porosity region(s) along the length of the stent 10. For example, a substantially round filament 30 can be flattened along a portion of the filament 30 that corresponds to the first porosity region 28 (e.g., the center region) of the stent 10. As shown in FIGS. 1-4 and 6, the first porosity region 28 is formed of filaments 30 that have a substantially flattened cross-sectional shape, sometimes referred to as a ribbon shape. Further, higher porosity regions of the filaments used in forming the stent (i.e., regions 24 and 26) can have a substantially round cross-sectional shape, which for example is the unaltered or natural shape of the filament. It is understood that any initial or unaltered cross-sectional shape can be utilized, so long as the shape allows for alteration of the filament cross-sectional shape such that the inscribed circle diameter 36 in regions of a stent formed with shape-altered filaments can be smaller than the inscribed circle diameter 36 in the regions formed of filaments that are not shape-altered. By way of example substantially rectangular, triangular, and round cross-sectional shapes can be used.

In some embodiments, the number of filaments 30 braided to form the stent 10 is uniform along the entire length of the stent 10. Additionally, the filaments 30 forming the stent 10 are continuous along the entire length of the stent 10, i.e., the filaments 30 found in the first porosity region 28 of the stent 10 are the same filaments 30 found in the second porosity 24, 26. As explained above, the only difference between the filaments in the first porosity region 28 and the second porosity regions 24, 26 is the cross-sectional shape of the filament 30.

Figure 5:
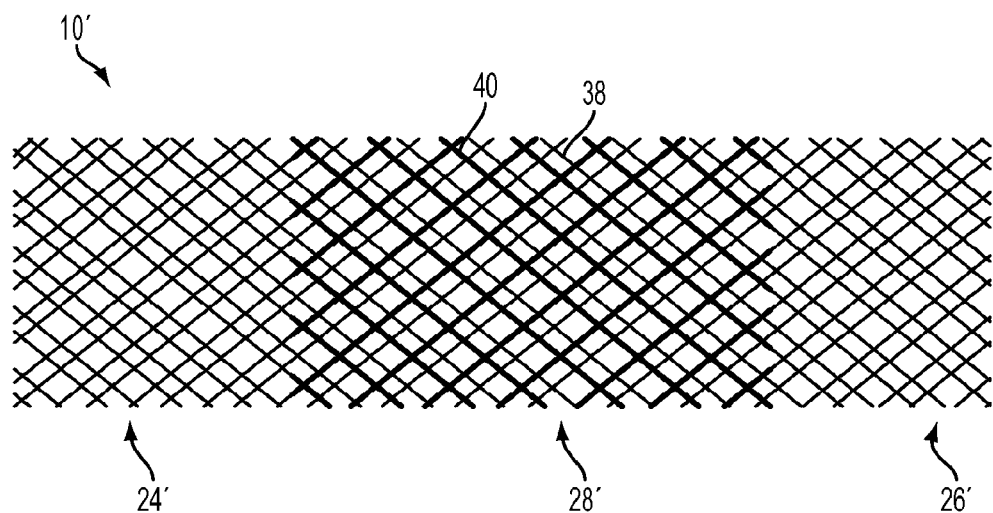
FIG. 5 is a partial cross-sectional view of another embodiment of an exemplary vascular occlusive device.

In the embodiments of FIGS. 1-4 the first or lower porosity region 28 is formed using filaments that are exclusively of an altered, i.e., substantially flattened cross-sectional shape. One skilled in the art will appreciate that the first of reduced porosity region can alternatively be formed using some filaments having an altered (such as flattened) cross-sectional shape together with other filaments having an unaltered shape, such as a rounded shape. FIG. 5 illustrates an example of such a stent where only some of the filaments used in forming the first or lower porosity region 28' of the stent 10' have an altered (e.g., flattened) cross-sectional shape. As is shown, the stent 10' has a first filament type 38 that has an unaltered and substantially constant cross-sectional shape along its length and a second filament type 40 that has at least two cross-sectional shapes along its length, an altered cross-sectional shape and an unaltered cross-sectional shape. The proportion of filaments altered to unaltered filaments in the first porosity region 28' can vary depending upon porosity characteristics desired for the stent. Generally, region 28' of stent 10' will have at least as many and typically more filaments with an altered cross-sectional shape in region 28'. For example, the filaments with an altered shape typically comprise about 50 percent to about 99 percent of the fibers in region 28'. More typically about 60 percent, about 70 percent, about 80 percent, or about 90 percent of the fibers in region 28' are those having an altered cross-sectional shape. Despite the stent 10' having filaments of different cross-sectional shapes within first porosity region 28', as in other embodiments, the number of filaments 38, 40 is uniform along the entire length of the stent 10' and the filaments 38, 40 themselves are continuous along the entire length of the stent 10', i.e., the filaments found in the center portion 28' of the stent are the same filaments 38, 40 found in the end portions 24', 26'.

Figure 6:
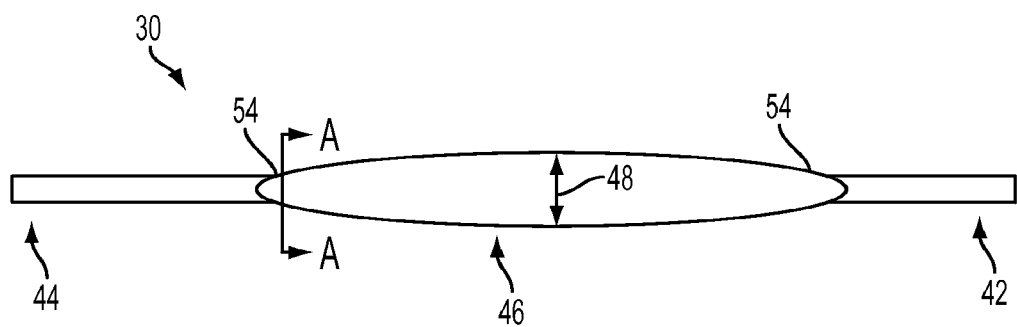
FIG. 6 is a top view of an exemplary filament for use in forming a vascular occlusive device.
Figure 7:
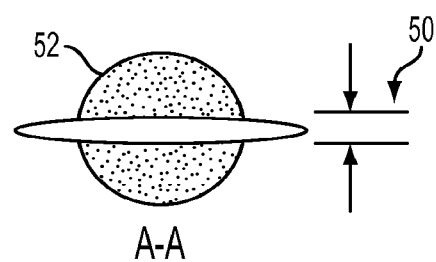
FIG. 7 is a cross-section view of the exemplary filament of FIG. 6 at Section A-A.

FIG. 6 illustrates an exemplary filament 30 used to form the braided stent 10. The filament has a first portion 42 and a second portion 44 having a rounded cross-sectional shape, which is the unaltered filament shape. Another region of filament 30, shown as middle portion 46 in FIG. 6, has an altered cross-sectional shape, i.e., a flattened or somewhat oval cross-sectional shape. The flattened portion 46 has a width 48 across the center of the flattened portion 46 that is wider than the diameter 52 of the adjacent round cross-section portions 42, 44. When a stent is formed using filament 30, the region braided with portion 46 will have a smaller inscribed diameter than regions braided with portions 42 and 44. By way of example, the width 48 can be in the range of about 0.001 inches to about 0.05 inches. FIG. 7 illustrates a cross-section of the filament 30 as viewed along line A-A of FIG. 6. As is shown, the flattened portion 46 will have a thickness 50 that is less than the diameter 52 of the round cross-section. The thickness 50 can be any desired thickness, for example the thickness 50 can be in the range of about 0.0003 inches to about 0.010 inches. The diameter 52 of the round cross-sectional portion of the filament can have any desired diameter, for example the diameter 52 can be in the range of about 0.0005 inches to about 0.0100 inches. The flattened middle portion 46 can have feathered ends 54 yielding a somewhat an oval shape when viewed from the top as is shown in FIG. 6. When braided, the flattened middle portion 46 of the filament 30 can be indexed about the region of the stent 10 that is to form the first or lower porosity region. For example, in the stent 10 shown in FIG. 3, the flattened portion 46 of the filaments 30 form the center region of the stent, which is the lower porosity region 28. The flattened middle portion 46 can have a length that will yield a center, lower porosity region of the stent that is large enough to cover the defect 14 to be treated but not so large as to occlude blood flow unnecessarily to adjacent vascular tissue.

One skilled in the art can readily determine the dimensions of a stent as deemed appropriate for a given application. The stent 10 can have a length that is so dimensioned as to stretch across a vascular defect 14. For example, the stent 10 length can be in the range of about 10 mm to about 100 mm.

The stent 10 can be self-expanding and radially compressible such that the stent 10 has a first, constrained diameter that is smaller than a second, unconstrained diameter that the stent assumes in its natural state. The unconstrained diameter should be so dimensioned as to be sufficiently larger than the vessel within which it is to be implanted to be safe and to maintain proper position. Generally, vessel 12 diameters will range from about 2 mm to about 5 mm and thus the stent 10 unconstrained outer diameter can be in the range of about 2.5 mm to about 5.5 mm, but the stent can have any desired diameter. The constrained diameter can be dimensioned for endovascular delivery, for example the constrained diameter can be in the range of about 0.01 inches to about 0.100 inches. Additionally, the stent 10 can be configured to provide structural support to the vessel 12 once placed in the vasculature in its expanded form. To aid in placement and blood flow, the ends 24, 26 of the stent 10 can be flared.

Self-expanding stents can be constructed from a variety of filament materials known to those skilled in the art. These materials include stainless steel, cobalt-chromium alloys, nickel, titanium, nitinol, and polymeric materials. Polymeric materials known to those skilled in the art can include, without limitation, shape memory polymers, silicone, polyethylenes, polyurethanes, polyethylene terephthalate (PET) polyesters, polyorthoesters, polyolefins, polyvinyls, polymethylacetates, polyamides, napthalane dicarboxylene derivatives, silks, polytetraflyouroethylenes, and polyanhydrides. The filament material can also be bioabsorbable or radiopaque, for instance by having an inner core formed of gold, platinum, iridium, or any other known radio-opaque material.

To effectively treat a defect, such as the aneurysms 14 shown in FIGS. 1 and 2, the stent 10 can have a variable porosity along the length of the tubular stent 10. For example, first porosity region 28 of the stent can be of a lower porosity than other regions of the stent, such as second porosity regions 24, 26. Although region 28 is shown to be disposed between regions 24 and 26, other arrangements of lower and higher porosity regions are possible. Additionally, the stent 10 can have multiple regions of lower porosity. For example, the stent 10 can have a distal region, proximal region, first center region, second center region, and third center region, wherein each region has a different porosity than the others (not shown). In any event, the lower porosity region can have a length that is sufficient to occlude flow to the defect, for example the length of the lower or first porosity region 28 can be in the range of about 5 mm to about 25 mm. In the embodiments illustrated in FIGS. 1-3, the center region 28 is configured to have a lower porosity and thus occlude blood flow to the neck 18 or walls 20, 22 of the aneurysm 14 and the proximal and distal regions 24, 26 are configured to allow blood flow and pressure without any substantial occlusion thereof to the adjacent perforator vessels 16.

The stent 10 can have a substantially constant number of picks-per-inch count along the length of the stent 10. For example, the picks-per-inch count in the region 24 can be the same as the picks-per-inch count in the region 26, which is the same as the picks-per-inch count in the region 28. For example, the picks-per-inch can be in the range of about 20 picks-per-inch to about 250 picks-per-inch.

As mentioned above, when braided, the filaments 30 forming the stent 10 can intersect to create polygonal mesh openings. The size of the polygonal mesh opening can then be measured by the inscribed circle diameter as described herein. The stent 10 can be formed so as to yield a first region having a first inscribed circle diameter (i.e., a first or lower porosity region) and a second region having a second inscribed circle diameter that is larger than the first inscribed circle diameter (i.e., a higher porosity region). Generally, the mesh openings of the first porosity region can have an inscribed circle diameter in the range of about 10 μm to about 500 μm and the mesh openings of the second porosity region can have an inscribed circle diameter in the range of about 400 μm to about 1000 μm.

Figure 8:
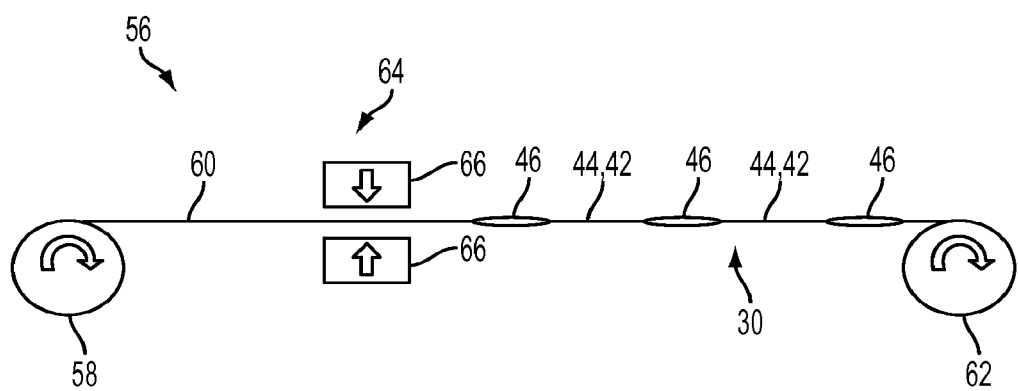
FIG. 8 is a schematic view of an exemplary system for forming exemplary filaments.

FIG. 8 illustrates an exemplary manufacturing system 56 to produce a filament 30 having alternating round and flat cross-sectional shapes. A supply spool 58 is first provided. The supply spool 58 should be wound with a supply filament 60 having a round cross-sectional shape. This can be formed of a typical stent filament material as described above and as is known in the art. The supply filament 60 from the supply spool 58 is then fed to a collection spool 62 configured to receive processed filament 30. Intermediate the supply spool 58 and collection spool 60, the supply filament 60 is fed through a press or stamping device 64, such as a pneumatic press. The press 64 can have a die set 66 that provides the means for altering (e.g., flattening) the filament 60. The die set 64 can be adjusted to control the thickness and length of the flattened section of filament 46 created by stamping the round supply filament 60 as it moves through the press 64. The press 64 can be configured to press any diameter of filament 60 and the die length, die pressure, die shims that control the thickness, and spool speed can be independently controlled and calibrated to produce the desired dimensions of the processed filament 30. Using this press 64, the supply filament 60 is pressed at set intervals to produce a filament 30 having alternating round 42, 44 and flat 46 cross-sectional shapes. The processed filament 30 is stored on the collection spool 62 once the filament is processed and ready to be braided.

Braiding of filaments 30 includes the interlacing of at least two sections of filament 30 such that the paths of the filament 30 sections are substantially diagonal to the stent 10 delivery direction, forming a tubular structure. Generally, braided stents can have a polygonal interstitial surface shape and can include a diamond braid having a 1/1 intersection repeat, a regular polygonal braid having a 2/2 intersection repeat, and a Hercules braid having a 3/3 intersection repeat. Moreover, a triaxial braid may also be used. A triaxial braid has at least one filament section that typically runs in the longitudinal direction or axial direction of the stent to limit filament movement. Moreover, an interlocking three-dimensional braided structure or a multi-layered braided structure can also be used. A multi-layered braided structure is defined as a structure formed by braiding wherein the structure has a plurality of distinct and discrete layers.

Figure 9:
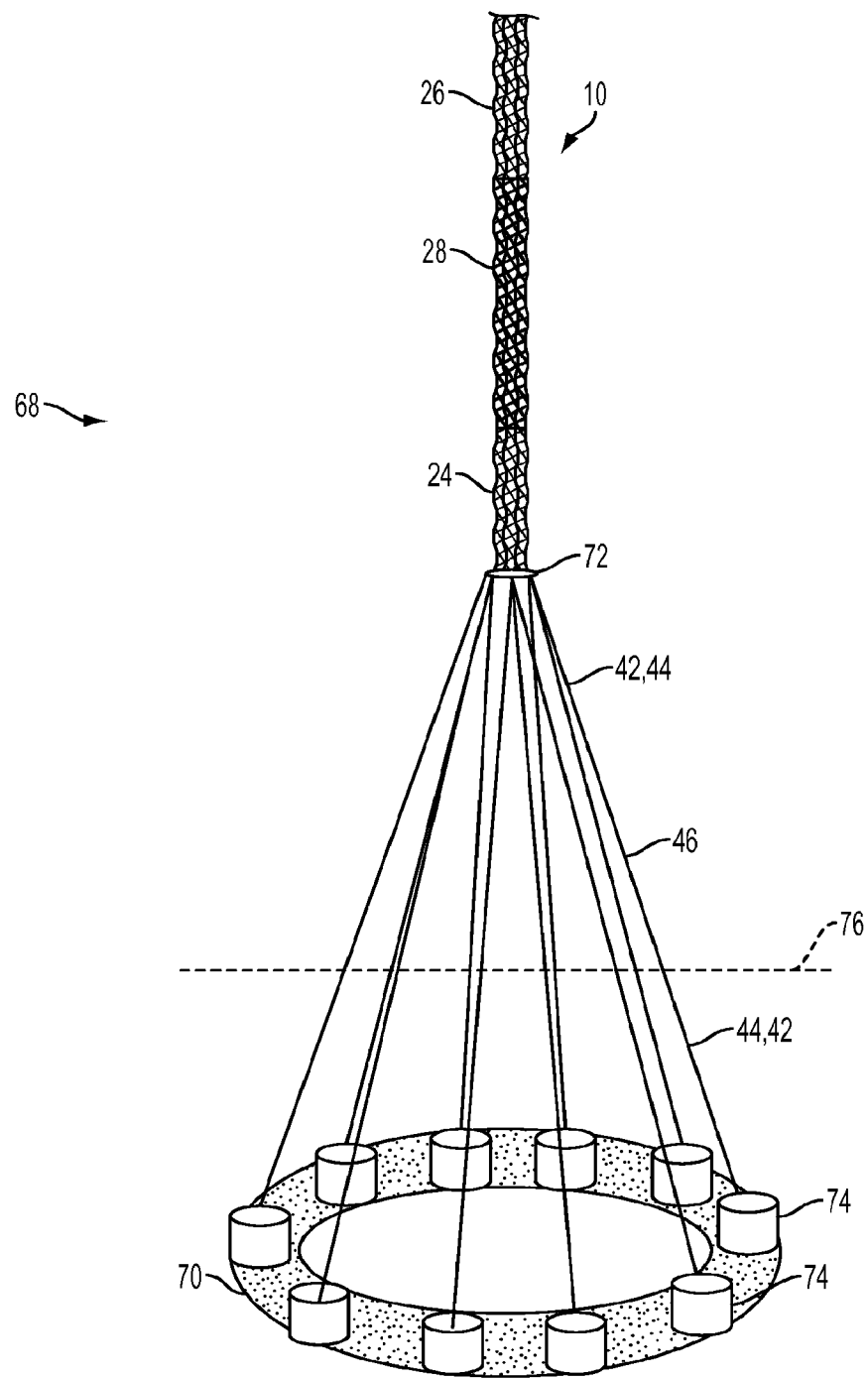
FIG. 9 is a schematic view of an exemplary braiding system.

FIG. 9 illustrates an exemplary braiding device 68. The braiding device 68 can have a spool loading mechanism 70 and a braiding mandrel 72 is first loaded with the desired filaments wound on spools 74 disposed in the spool loading mechanism 70. For example, the collection spools 62 of processed filaments 30 can be loaded into the braiding machine 68. The collection spools 62 used in the braiding machine 68 can have filaments 30 with flattened cross-sectional shapes as described above, filaments 60 with round cross-sectional shapes, or combinations of both. If only collection spools 62 having flattened cross-sectional shapes are utilized, the resulting stent 10 can be of the form shown in FIGS. 1-4. If a combination of collection spools 62 having flattened cross-sectional shapes and spools having a round cross-sectional shape are used, then the resulting stent 10' can be of the form shown in FIG. 5. The collection spools 62 should be indexed in the braid machine 68 so that any flattened portions 46 of the filaments on the collection spools corresponds to a desired region of lower porosity in the resulting stent 28. For example, the collection spools 62 can be indexed so that the flattened portion is indexed to an indexing line 76 such that the flat portion 46 of the filament 30 corresponds to the center region 28 of the stent intermediate the end portions 24, 26 of the stent. The braided stent 10 can be cut to length distally of the braiding mandrel 72.

Alternatively, the region of lower porosity can have more filaments or more picks per inch than the region of higher porosity. But, by changing only the cross-sectional shape of the filaments and keeping the number of filaments and picks per inch uniform along the length of the stent, manufacturing can be simplified as the braiding process is uncomplicated by changing the number of filaments or braiding pattern during the braiding process. Thus, a preferred embodiment is one that has a uniform filament count and picks per inch along the entire length of the stent.

As mentioned, the mesh density, and therefore the porosity, can also depend on the braid angle. Generally, the braid angle is defined as the angle between crossing filaments at a braid pick. Typically three braid angles are relevant: the braid angle during construction on a braiding machine, the braid angle when the stent is unconstrained, and the braid angle when the stent is constrained. The braid angle during construction is generally larger than the unconstrained and constrained braid angle. The braided structure is formed having a braid angle from about 30° to about 150° with respect to the longitudinal axis of the braided structure.

When deploying the stent 10 into a vessel 12, the braid angle is reduced as the stent 10 is compressed radially to fit into the vessel 12. The braid angle then expands when the stent 10 moves from the constrained position to its unconstrained position. Preferably, the stent 10 will be formed such that the braid angle is uniform along the length of the tubular member 10 when the tubular member 10 is either entirely constrained or unconstrained, such that the braid angle in the first length is the same as the braid angle in the second length.

A person skilled in the art will appreciate that the present invention has application in conventional minimally-invasive and open surgical instrumentation as well application in robotic-assisted surgery. While in many cases the description uses cranial vasculature, aneurysms, and stents configured for the treatment thereof as an exemplary delivery location and implant, this is by way of illustration only. The methods and devices described herein can be applied to virtually any vasculature, defect, and intravascular implant.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method of manufacturing a tubular intravascular implant, comprising:
   providing a plurality of supply spools, each having a supply of a filament having a round cross-sectional shape;
   advancing the filaments on each supply spool to a corresponding collection spool;
   deforming a selected number of the filaments in a selected region thereof at selected intervals between the supply spools and the collection spools such that at least some of the collection spools have filaments with a round cross-sectional shape and a flattened cross-sectional shape, the selected number of the filaments deformed being less than all of the filaments in the selected region thereof;
   utilizing the filaments in the collection spools in a filament braiding device to form a tubular member with an outer surface defined by the braided filaments, the tubular member having a length with regions of a first, lower porosity and regions of a second, higher porosity; and
   cutting the tubular member to form a plurality of intravascular stents, each individual stent having a first length region of a first, lower porosity characterized by the presence of filaments having a flattened cross-sectional shape and filaments having a rounded cross-sectional shape, each individual stent having at least one second length region of a second, higher porosity characterized by the presence of filaments having a rounded cross-sectional shape.

2. The method of claim 1, wherein all of the collection spools have filaments with a flattened cross-sectional shape.

3. The method of claim 1, wherein the tubular member formed in the filament braiding device is formed with a constant pick count throughout its length.

4. The method of claim 1, wherein cutting the tubular member includes cutting the tubular member such that the first length region of each individual stent is at an intermediate portion of the individual stent proximal to a distal end of the individual stent and distal to a proximal end of the individual stent.

5. The method of claim 4, wherein the at least one second length region of each individual stent is adjacent to the distal end of the individual stent.

6. The method of claim 4, wherein the at least one second length region is adjacent to the proximal end of the individual stent.

7. The method of claim 1, wherein cutting the tubular member includes cutting the tubular member such that the first length region of each individual stent extends over a distance in the range of about 5 mm to about 25 mm.

8. The method of claim 1, wherein deforming the filaments to create the filaments with the flattened cross-sectional shape includes deforming the filaments such that the flattened cross-sectional shape has a length, a width, and a thickness, and the width is greater than the thickness and less than the length of the filaments.

9. The method of claim 1, wherein deforming the filaments to create the filaments with the flattened cross-sectional shape includes flattening a width of the filaments in the range of about 0.001 inches to about 0.05 inches.

10. The method of claim 1, wherein cutting the tubular member includes cutting each individual stent to have a number of filaments in the range of 8 to 288.

11. The method of claim 1, wherein cutting the tubular member includes cutting each individual stent to have a number of filaments selected from the group consisting of 8, 16, 32, 48, 64, 72, 96, 120, 144, 192, and 288.

* * * * *